(12) United States Patent
Alperin

(10) Patent No.: US 12,326,869 B1
(45) Date of Patent: Jun. 10, 2025

(54) SYSTEM AND METHODS FOR DELIVERING CONTEXTUAL RESPONSES THROUGH DYNAMIC INTEGRATIONS OF DIGITAL INFORMATION REPOSITORIES WITH INQUIRIES

(71) Applicant: SurvivorNet, Inc., New York, NY (US)

(72) Inventor: Steven David Alperin, New York, NY (US)

(73) Assignee: SurvivorNet, Inc., New York, NY (US)

( * ) Notice: Subject to any disclaimer, the term of this patent is extended or adjusted under 35 U.S.C. 154(b) by 0 days.

(21) Appl. No.: 18/762,268

(22) Filed: Jul. 2, 2024

(51) Int. Cl.
G06F 16/00 (2019.01)
G06F 16/248 (2019.01)
(Continued)

(52) U.S. Cl.
CPC ........ G06F 16/248 (2019.01); G06F 16/3329 (2019.01); G06F 16/9024 (2019.01);
(Continued)

(58) Field of Classification Search
CPC ............... G06F 16/248; G06F 16/9024; G06F 16/3329; G06F 9/542; G06F 17/18;
(Continued)

(56) References Cited

U.S. PATENT DOCUMENTS 10,332,622 B2 6/2019 Campbell et al.
10,553,308 B2 * 2/2020 Baldwin ................. G06F 40/30
(Continued)

FOREIGN PATENT DOCUMENTS

CA 3082239 A1 * 12/2020
IN 202121054099 A 11/2024
(Continued)

OTHER PUBLICATIONS

Raza Nowrozy et al., "Towards a Universal Privacy Model for Electronic Health Record Systems: An Ontology and Machine Learning Approach", Informatics 2023, 10, 60, Published: Jul. 11, 2023, pp. 2-28.*

(Continued)

Primary Examiner — Srirama Channavajjala
(74) Attorney, Agent, or Firm — Caldwell Intellectual Property Law

(57) ABSTRACT

A system for delivering contextual responses through dynamic integrations of digital information repositories with inquiries, comprising a computing device configured to collect a plurality of inquiries associated with an entity, access a plurality of digital information repositories in communication with the at least a processor to retrieve a plurality of entity records pertaining to the entity, extract one or more entity features from the plurality of inquiries and the plurality of entity records, implement a nested data storage structure to store the plurality of inquiries and the plurality of entity records based on the one or more entity features, generate, at one or more process modules interfaced with the computing device, one or more contextual responses upon receipt of an additional inquiry by traversing the nested data storage structure, and display the one or more contextual responses to the entity through a user interface at a display device.

18 Claims, 8 Drawing Sheets

(51) Int. Cl.
*G06F 16/3329* (2025.01)
*G06F 16/901* (2019.01)
*G06N 3/04* (2023.01)
*G06N 5/022* (2023.01)
*G06N 20/00* (2019.01)
*G06N 20/10* (2019.01)
*G16H 10/60* (2018.01)

(52) U.S. Cl.
CPC ............... *G06N 3/04* (2013.01); *G06N 5/022* (2013.01); *G06N 20/00* (2019.01); *G06N 20/10* (2019.01); *G16H 10/60* (2018.01)

(58) Field of Classification Search
CPC ........ G16H 10/60; G16H 15/00; G16H 50/20; G16H 50/30; G06N 20/00; G06N 20/10; G06N 5/022; G06N 3/04
See application file for complete search history.

(56) References Cited

U.S. PATENT DOCUMENTS

| | | | |
|---|---|---|---|
| 10,566,081 B2 | 2/2020 | Hao et al. | |
| 10,586,615 B2* | 3/2020 | Bastide | G16H 10/20 |
| 11,272,649 B2 | 3/2022 | Jarosz | |
| 2012/0065987 A1* | 3/2012 | Farooq | G16H 50/70 |
| | | | 705/2 |
| 2016/0283662 A1 | 9/2016 | Batta | |
| 2018/0293462 A1* | 10/2018 | Ambati | G06N 5/022 |
| 2021/0110351 A1* | 4/2021 | Wang | G16H 10/20 |
| 2021/0295996 A1* | 9/2021 | Goetz | G06F 9/542 |
| 2021/0319387 A1* | 10/2021 | Denton | G16H 50/30 |
| 2021/0357808 A1* | 11/2021 | Tsuyuki | G06F 18/2178 |
| 2022/0181029 A1* | 6/2022 | Colley | G06V 30/416 |
| 2024/0169714 A1* | 5/2024 | AlRegib | G16H 30/20 |
| 2024/0221949 A1* | 7/2024 | Godbole | G16H 50/20 |

FOREIGN PATENT DOCUMENTS

WO  WO2019229528 A2 * 12/2019
WO  WO2020237156 A1 * 11/2020

OTHER PUBLICATIONS

Divyanshu Singh et al., "Prediction of Adverse Effects of Medical Treatment using Electronic Health Record and Machine Learning" 2021 Asian Conference on Innovation in Technology (ASIANCON), Oct. 2021, pp.*

B. Aldughayfiq et al; "Capturing Semantic Relationships in Electronic Health Records Using Knowledge Graphs: An Implementation Using MIMIC III Dataset and GraphDB"; Published: Jun. 15, 2023; https://www.mdpi.com/2227-9032/11/12/1762.

* cited by examiner

SYSTEM AND METHODS FOR DELIVERING CONTEXTUAL RESPONSES THROUGH DYNAMIC INTEGRATIONS OF DIGITAL INFORMATION REPOSITORIES WITH INQUIRIES

FIELD OF THE INVENTION

The present invention generally relates to the field of data processing system and machine learning. In particular, the present invention is directed to a system and methods for delivering contextual responses through dynamic integrations of digital information repositories with inquiries.

BACKGROUND

Implementation of real-time data analysis with large volumes of data from diverse sources remains challenging in many industries where the evolving nature of data or specific contexts of user inquiries can greatly affect subsequent decision-making process. Electronic health records (EHRs), customer relationship management (CRM) systems, and other similar databases store vast amounts of data but typically lack the capability of dynamically integrating stored data with real-time inquiries, resulting in outdated or irrelevant responses.

SUMMARY OF THE DISCLOSURE

In an aspect, a system for delivering contextual responses through dynamic integrations of digital information repositories with inquiries is described. The system includes a computing device having at least a processor and a memory communicatively connected to the at least a processor, wherein the memory contains instructions configuring the at least a processor to collect a plurality of inquiries associated with an entity, access a plurality of digital information repositories in communication with the at least a processor to retrieve a plurality of entity records pertaining to the entity, extract one or more entity features from the plurality of inquiries and the plurality of entity records, implement a nested data storage structure to store the plurality of inquiries and the plurality of entity records based on the one or more entity features, generate, at one or more process modules interfaced with the at least a processor, one or more contextual responses upon receipt of an additional inquiry by traversing the nested data storage structure, and display the one or more contextual responses to the entity through a user interface at a display device.

In another aspect, a method for delivering contextual responses through dynamic integrations of digital information repositories with inquiries is described. The method includes collecting, by at least a processor, a plurality of inquiries associated with an entity, accessing, by the at least a processor, a plurality of digital information repositories in communication with the at least a processor to retrieve a plurality of entity records pertaining to the entity, extracting, by the at least a processor, one or more entity features from the plurality of inquiries and the plurality of entity records, implementing, by the at least a processor, a nested data storage structure to store the plurality of inquiries and the plurality of entity records based on the one or more entity features, generating, by the at least a processor, one or more contextual responses, at one or more process modules interfaced with the at least a processor, upon receipt of an additional inquiry by traversing the nested data storage structure, and displaying, by the at least a processor, the one or more contextual responses to the entity through a user interface at a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to a system and methods for delivering contextual responses through dynamic integrations of digital information repositories with inquiries. The system includes a computing device having at least a processor and a memory communicatively connected to the at least a processor, wherein the memory contains instructions configuring the at least a processor to collect a plurality of inquiries associated with an entity, access a plurality of digital information repositories in communication with the at least a processor to retrieve a plurality of entity records pertaining to the entity, extract one or more entity features from the plurality of inquiries and the plurality of entity records, implement a nested data storage structure to store the plurality of inquiries and the plurality of entity records based on the one or more entity features, generate, at one or more process modules interfaced with the at least a processor, one or more contextual responses upon receipt of an additional inquiry by traversing the nested data storage structure, and display the one or more contextual responses to the entity through a user interface at a display device. Exemplary embodiments illustrating aspects of the present disclosure are described below in the context of several specific examples.

Figure 1:
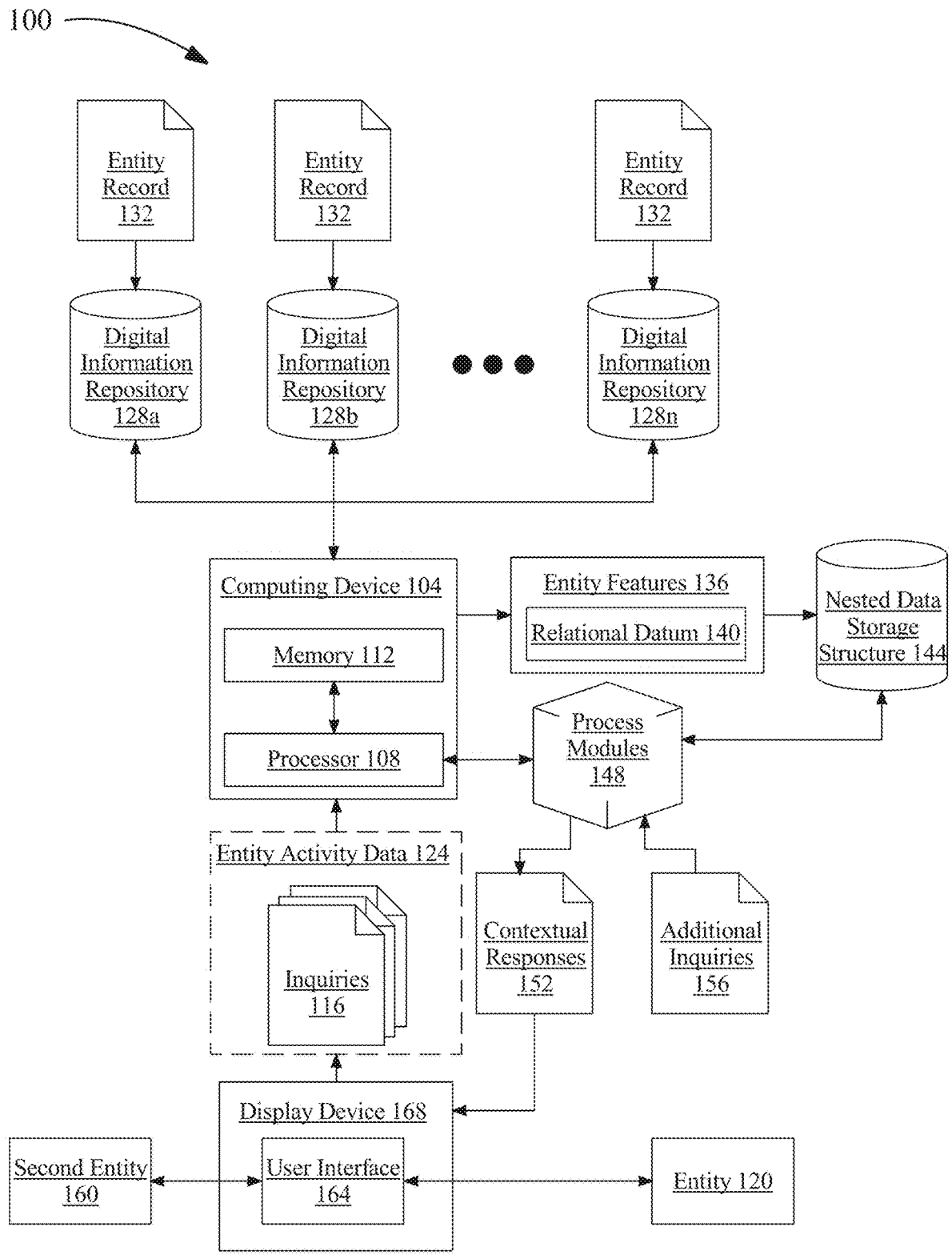
FIG. 1 is a block diagram of an exemplary embodiment of an apparatus for delivering contextual responses through dynamic integrations of digital information repositories with inquiries.

Referring now to FIG. 1, an exemplary embodiment of a system 100 for delivering contextual responses through dynamic integrations of digital information is illustrated. System 100 includes a computing device 104. Computing device 104 includes at least a processor 108 communicatively connected to a memory 112. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, at least a processor 108 is configured to collect a plurality of inquiries 116 associated with an entity 120. As used in this disclosure, an "inquiry" is a datum representing a request for information, data submissions, queries, or other forms of interaction initiated by an entity seeking to retrieve, process, or interact with system 100. In some cases, entity 120 may include, without limitation, an individual user, a group of users, a system or a subsystem, an organization, a computer program or a software, or any other identifiable unit interacting within system 100. In one embodiment, plurality of inquiries 116 may include textural inquiries. As a non-limiting example, plurality of inquiries 116 may include one or more text-based questions, comments, or commands entered through a user device (i.e., any device a user uses to interact with system 100, such as smartphone, laptop, desktop, or the like) using a keyboard, touchscreen, or voice-to text technology. In yet another embodiment, plurality of inquiries 116 may include one or more references to a plurality of images or other attached documents. In yet another embodiment, plurality of inquiries 116 may include voice inquiries, for example, and without limitation, spoken requests or questions may be captured via a microphone and processed using speech recognition techniques to convert spoken language into machine-readable text. In some embodiments, plurality of inquiries 116 may be collected through one or more digital forms on websites or connected applications. In some cases, entity 120 may fill out fields with specific information requests or data. Such collection process, in some cases, may be interactive; for instance, plurality of inquiries 116 may include dynamic inquiries occurred during one or more interactive sessions e.g., live chats with one or more chatbot or virtual assistants. As a non-limiting example, plurality of inquiries 116 may include a web browser browsing history, a chat history, or a transcript of a video/audio call recording.

With continued reference to FIG. 1, in some cases, plurality of inquiries 116 may be organized and formatted in a predictable, predefined manner. In an embodiment, each inquiry of plurality of inquiries may include a structured data input describing at least one user-generated question. For example, and without limitations, plurality of inquiries 116 may be characterized by presence of identifiable input fields within the collected data, wherein the identifiable input fields may include specific types of information entered into set categories or parameters. In some cases, structured data input may be used to directly query digital information repositories as described in further detail below. As used in this disclosure, a "user-generated question" is a query formulated and submitted by a user. In one or more embodiments, plurality of inquiries 116 may include search queries entered into a web interface or an integrated digital health application. In some cases, system 100 as described herein may be a plugin integrated in a web browser or other third party application; for instance, and without limitation, plurality of inquiries 116 may be collected while user entering one or more search queries or accessing one or more application programming interfaces (API requests) as at least a processor 108 may, at least in part, monitoring user interactions within such integrated computing environment. As a non-limiting example, plurality of inquiries 116 may include a query about "cancer" submitted by a patient through a web browser. In some cases, plurality of inquiries 116 may include a record of historical search results, such as a collection of URLs patent has accessed or webpages containing contents related to the query (e.g., possible symptoms, outcome, or treatment related to cancer) patient has viewed. Additionally, or alternatively, plurality of inquiries 116 may be received using a chatbot, as described herein below.

With continued reference to FIG. 1, in other embodiments, plurality of inquiries 116 may include a structured data output describing at least one system-generated questions, wherein the "system-generated questions," for the purpose of this disclosure, are queries or prompts that are automatically created and issued by a computing environment or system based on one or more predefined computational rules, algorithms, or responses to user interactions. In some cases, unlike user-generated questions as described above, system-generated questions may be formulated by web browsers or integrated software applications to facilitate further interactions. As a non-limiting example, plurality of inquiries 116 may include one or more follow-up questions that narrows down options or clarifies search queries entered by entity 120 e.g., "Are you currently on any medication?" For instance, and without limitation, plurality of inquiries 116 may include any set of inquiries or queries, as described in U.S. patent application Ser. No. 18/536,623, filed on Dec. 12, 2023, entitled "APPARATUS AND A METHOD FOR GENERATING A USER REPORT," U.S. patent application Ser. No. 18/426,617, filed on Jan. 30, 2024, entitled "APPARATUS AND METHOD FOR GENERATING A TEXT OUTPUT," and U.S. patent application Ser. No. 18/615,984, filed on Mar. 25, 2024, entitled "APPARATUS AND METHOD FOR LOCATION MONITORING," which are incorporated herein by reference in their entirety.

With continued reference to FIG. 1, additionally, or alternatively, collecting plurality of inquiries 116 may include generating plurality of inquiries 116 as a function of entity activity data 124 pertaining to entity 120. As described in this disclosure, "entity activity data" is a set of recorded actions, behaviors, interactions, or transactions performed by entity 120. As a non-limiting example, entity activity data 124 may include browsing history, purchase records, device usage patterns, service requests, social media activities, or any other user engagement that entity 120 has with system 100 or integrated computing environment. In some cases, collecting plurality of inquiries 116 may include gathered from web analytics, mobile app usage, sensor outputs, customer relationship management (CRM) systems, among others. In some cases, entity activity data 124 may include one or more timestamps, geographical locations, frequency or activities, duration, description of interactions, and/or the like. For instance, and without limitation, entity activity data 124 may include user data having at least a datum associated with a user's frequented location when performing the interactions (e.g., home address), such as any situational location data as described in U.S. patent application Ser. No. 18/615,984. Plurality of inquiries 116 derived from entity activity data 124 may include system-generated questions formulated based on data related to patterns, needs, or issues indicated through entity's 120 interactions and behaviors. As a non-limiting example, if an integrated health monitoring application detects irregular activity data suggestive of a symptom, at least a processor 108 may be configured to generate a question like "Have you been experiencing discomfort or pain."

With continued reference to FIG. 1, in some cases, one or more submissions may be converted into plurality of inquiries 116 or entity record as described below in a machine-encoded or machine-readable format through optical character recognition or an optical character reader (OCR). In some cases, submissions may include one or more uploaded electronic file along with plurality of inquiries 116. In some cases, plurality of inquiries 116 may be incorporated inside one or more uploaded files. For example, and without limitation, at least a processor 108 may perform automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

With continued reference to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

With continued reference to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

With continued reference to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

With continued reference to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2-4. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

With continued reference to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2-4.

With continued reference to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, system 100 is configured to access a plurality of digital information repositories 128*a-n* in communication with the at least a processor 108 to retrieve a plurality of entity records 132 pertaining to entity 120. As used in this disclosure, a "digital information repository" is a system designed to house, manage, and manipulate digital data. A "entity record," for the purpose of this disclosure, is a set of one or more data entries in a digital information repository that represent an individual entity. In one embodiment, digital information repository may include a storage system or database configured to support the retrieval, removal, and modification of information in digital formats by authorized users. As a non-limiting example, digital information repositories 128*a-n* may include any structured database containing data organized in a way that at least a processor 108 may effectively search or index information related to a plurality of entities that preserved accurately over time. Each entity record of plurality of entity records 132 may include one or more attributes describing one or more characteristics, behaviors, status, and other metadata relevant to an individual entity; for instance, and without limitation, an entity record may include personal identification information of a person, operational statistics for a device, financial data for a company, and/or the like. In some cases, entity records 132 may be derived from plurality of inquiries 116; for example, and without limitation, entity 120 may submit one or more inquiries along with information associated with entity records 132 as described below with reference to FIG. 5.

With continued reference to FIG. 1, in some cases, digital information repositories 128a-n may be accessed, and plurality of private records 132 may be retrieved, as a function of one or more identifiable data associated with entity 120. In some cases, data that may be considered identifiable if the identity of entity 120, such as, without limitation, a user, a patient, or a participant is known or may readily be ascertained. Exemplary identifiable data, such as, without limitation, username, patient ID, social security numbers, or any other linkable variables recognized from one or more inquiries of plurality of inquiries 116 that directly or indirectly identifies an entity, may be used to access one or more digital information repositories connected to computing device 104 and retrieve, from the accessed digital information repositories, one or more entity records associated with the identified entity. In some cases, entity records retraval may be simultaneous to the reception of inquiries. As inquiries are received, system 100 may concurrently access relevant digital information repositories to fetch corresponding entity records through APIs.

With continued reference to FIG. 1, in some cases, entity record may include private, sensitive information pertaining to entity 120 which are protected according to privacy regulations, and access to such entity record may be controlled to prevent unauthorized use. As a non-limiting example, plurality of digital information repositories 128a-n may include an electronic health records (EHR) system used by healthcare providers, wherein the EHR system may include a plurality of entity records such as electronic health records associated with plurality of entities. As used in this disclosure, an "electronic health record" is an electronic version of a patient's medical history. In some cases, such entity records may include data describing detailed diagnoses, treatment outcomes, physician notes, among others. As another non-limiting example, digital information repository may be a customer relationship management (CRM) system that stores plurality of entity records 132, such as records for each customer, contact information, purchase histories, interaction logs, customer preferences, and/or the like. In yet another non-limiting example, plurality of digital information repositories may include one or more financial services database containing individual account records associated with different entities, wherein each individual account record may include details such as account balances, transaction history, account holder information, credit scores, and/or the like. As a further non-limiting example, digital information repositories 128a-n may include a learning management system (LMS) containing a plurality of student profiles detailing enrollment requirements, student grades, course completion status, instructor feedbacks, and/or the like. As a person skilled in the art, upon reviewing the entirety of this disclosure, will be aware of various type of digital information repositories at least a processor 108 may communicate with, and the diverse entity records that may be maintained, accessed, and manipulated within these repositories.

With continued reference to FIG. 1, in a non-limiting embodiment, digital information repository may include a database communicatively connected to at least a processor 108. In some cases, database may be local to computing device 104. In other cases, database may be remote to computing device 108 and communicative with at least a processor 108 by way of one or more networks, such as, a cloud network, a mesh network, or the like. By way of example, a "cloud-based" system, as used herein, is a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure at least a processor 108 connects directly, dynamically, and non-hierarchically to as many other computing devices as possible. A "network topology" as used in this disclosure is an arrangement of elements of a communication network.

With continued reference to FIG. 1, in some cases, a digital information repository may be implemented, without limitation, as a relational database, a key-value retrieval database such as a NOSQL database, or any other format or structure for use as a database that a person skilled in the art would recognize as suitable upon review of the entirety of this disclosure. One or more digital information repositories may alternatively or additionally be implemented using a distributed data storage protocol and/or data structure, such as a distributed hash table or the like. In some cases, plurality of entity records 132 in plurality of digital information repositories 128a-n may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which entity records and data entries thereof in digital information repositories may store, retrieve, organize, and/or reflect data and/or records as used herein, as well as categories and/or populations of data consistently with this disclosure.

With continued reference to FIG. 1, at least a processor 108 may compile a first database containing plurality of inquiries 116 and a second database containing plurality of entity records 132 pertaining to entity 120. In some cases, first database may be configured to store and manage user-generated and/or system-generated inquiries, such as, without limitation, text inputs, voice commands, electronic forms, browsing histories, chat record, or any other interactive session logs that capture one or more interactions between entity 120 and system 100, while second database may be configured to store and manage entity records associated with entity 120 i.e., an array of data points, such as, without limitation, personal information, transaction histories, activity logs, and any other pertinent records that define entity 120 and entity's 120 interactions within system 100.

With continued reference to FIG. 1, in one or more embodiments, first database may be implemented to efficiently handle both structured and unstructured data. Compiling first database may include appending, for each inquiry of plurality of inquiries 116, metadata such as identifiable data as described above e.g., a username or a patient ID that is currently available to the ongoing session. In some cases, at least a processor 108 may be configured to initialize, for each database, a local storage, or a session storage respectively for real-time data handling, given that inquiries and entity records may be time-sensitive. In some cases, compiling first database and second database may include synchronize data between databases, for example, and without limitation, updates in entity records may be reflected in how inquiries are handled and vice versa. Discrepancies or inconsistencies between databases may also be corrected, by at least a processor 108, through the cross-database data synchronization.

With continued reference to FIG. 1, in one or more embodiments, plurality of entity records 132 may include contextual data. As used in this disclosure, "contextual data" is additional information related to the background, environment, or circumstances relevant to a specific data points or events. In some cases, contextual data may complement primary data i.e., plurality of inquiries 116, for example, and without limitation, plurality of entity records 132 may include patient location data providing context to one or more medical questions by revealing environmental factors or accessibility to nearby healthcare facilities, or as another example, time of day for symptom reporting indicative of circadian patterns of symptoms or medication effectiveness e.g., higher pain reports during cold mornings. For instance, and without limitation, contextual data may include any contextual data as described in U.S. patent application Ser. No. 18/426,617. Additionally, or alternatively, plurality of entity records 132 may be entered into a computing device or digital information repositories 128*a-n* by being uploaded by entity 120 or other persons such as professionals in related field using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a processor 108 may automatically obtain entity records using such an identifier, for instance by submitting a request to digital information repository e.g., a compendium of documents such as JSTOR as provided by Ithaka Harbors, Inc. of New York.

With continued reference to FIG. 1, at least a processor 108 is configured to extract one or more entity features 136 from plurality of inquiries 116 and plurality of entity records 132. As used in this disclosure, an "entity feature" is an attribute or characteristic derived from datasets associated with an entity, identifiable and extractable through analysis of data elements contained within the datasets. In one embodiment, entity features 136 may be representative of one or more aspects of entity's behavior, status, interactions, or preference as manifested in collected inquiries and entity records. In some cases, each entity feature may be quantifiable or qualifiable trait that can be explicitly measured, observed, or inferred from compiled databases as described above, and is capable of being stored, processed, and utilized independently or in conjunction with other features within system 100 as described in further detail below. Exemplary entity features may include, without limitation, geographical location, product purchased, frequency of purchases, specific health indicators (e.g., blood pressure readings, glucose levels, heart rate data, and the like), usage patterns (e.g., frequency and duration of usage of system 100 or other integrated software application or digital services), number of questions, types of inquiries made, average resolution times, travel patterns, and/or the like.

With continued reference to FIG. 1, in one or more embodiments, extracting one or more entity features 136 may include extracting a set of inquiry features from plurality of inquiries 116, extracting a set of record features from plurality of entity records 132, and identifying one or more entity features 136 by correlating the set of inquiry features and the set of record features. As used in this disclosure, an "inquiry feature" is an attribute derived from plurality of inquiries 116. In some cases, exemplary inquiry feature may include, without limitation, textural content of the inquiry, frequency of specific queries, timestamps, and user interaction metrics such as click-through rates or session durations, among others. A "record feature," for the purpose of this disclosure, is an attribute or characteristic derived from plurality of records 132. In some cases, exemplary record feature may include, without limitation, transaction histories, demographic data, user preferences, historical interaction patterns, current health status, and/or the like.

With continued reference to FIG. 1, in some cases, at least a processor 108 may be configured to parse and analyze the data contained within each inquiry of plurality of inquiries 116 received by system 100. In one or more embodiments, one or more natural language processing techniques may be implemented to identify key terms, categories, and/or data patterns within plurality of inquiries 116, for instance, and without limitation, extracting set of inquiry features from plurality of inquiries 116 may include extracting, using a language processing module, types of questions asked, language sentiment, urgency, and/or the like from plurality of inquiries 116. Language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well, Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

With continued reference to FIG. 1, language processing module may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations. Alternatively, or additionally, language processing module may be produced using one or more large language models (LLMs) as described in further detail below.

With continued reference to FIG. 1, in some cases, record feature extraction may be executed, using one or more natural language processing models, in parallel to inquiry feature extraction. In an embodiment, significant data points such as, without limitation, entity's EHRs, historical interactions, transactions, or status changes may be extracted. One or more entity features 136 may then be identified by correlating set of inquiry features and set of record features. In some cases, each entity feature may include at least a relational datum 140. As used in this disclosure, a "relational datum" is a specific piece of data that establishes a connection, relationship, or linkage between two or more entity features. In some cases, relational datum 140 may characterize an interdependency, association, or otherwise a correlation that exist among one or more entity features 136. In one or more embodiments, relational datum 140 may exist between two interrelated entity feature. As a non-limiting example, a first entity feature may include a patient medication adherence feature measuring how consistently a patient follows his/her prescribed medication regimen, quantified by tracking the timing and dosage of medication taken from patient's EHR, may include a relational datum that connects the first entity feature with a second entity feature, for example, a health outcome improvement feature that tracks changes in patient's health status over time (e.g., reductions in symptom severity or improvement in one or more related biomarkers), wherein the relational datum may include a correlation coefficient that quantifies a relationship between medication adherence and health outcome improvements. In some cases, a high correlation coefficient may indicate that certain degree of adherence to medication closely aligns with significant improvements in patient's health outcome, while a low correlation coefficient may indicate that certain degree of adherence of medication may be less irrelevant to improved patient's health outcome. Additionally, or alternatively, one or more machine-learning processes as described in further detail below may be used to predict relational datum 140 based on correlated features.

With continued reference to FIG. 1, in some embodiments, entity features may be extracted using a feature learning algorithm. A "feature learning algorithm," as used herein, is a machine-learning algorithm that identifies associations between elements of data in a data set, which may include without limitation a training data set, where particular outputs and/or inputs are not specified. For instance, and without limitation, a feature learning algorithm may detect co-occurrences of elements of data, as defined above, with each other. As a non-limiting example, feature learning algorithm may detect co-occurrences of elements, as defined above, with each other. Computing device may perform a feature learning algorithm by dividing elements or sets of data into various sub-combinations of such data to create new elements of data and evaluate which elements of data tend to co-occur with which other elements. In an embodiment, first feature learning algorithm may perform clustering of data.

With continued reference to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device may generate a k-means clustering algorithm receiving unclassified data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\text{argmin}_{c_i \in C} \text{dist}(c_i, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $c_i = 1/|S_i| \Sigma x_i \ni S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between a elements to be compared and/or clustered and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between an element and the data entry cluster. Alternatively, or additionally k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; persons skilled in the art, upon reviewing the entirety of this disclosure, will be aware of various additional or alternative feature learning approaches that may be used consistently with this disclosure.

With continued reference to FIG. 1, as a non-limiting example, language processing module as described herein may use a corpus of documents e.g., plurality of inquiries 116 and plurality of entity records 132 to generate associations between entity features 136 to analyze set of inquiry features extracted from plurality of inquiries and set of record features extracted from plurality of entity records 132 and determine that correlation between inquiry features and record features indicate the significance of certain relationships or patterns. For instance, language processing module may discover a strong correlation between a frequency of inquiries about specific symptoms (i.e., inquiry features) and documented outcomes of particular treatments (i.e., record features) within the health records. Such correlation may suggest a significant relationship between the symptoms mentioned in patient inquiries and the effectiveness of certain treatments. In some cases, language module and/or at least a processor 108 may perform such analysis using a selected set or subset of significant documents, such as one or more inquiries or records identified manually by one or more experts, or evaluated automatically by one or more pre-determined criteria, as representing good information. As a non-limiting example, at least a processor 108 may extract entity features that reflect both the real-time user interactions (as captured in the inquiries) and the historical context (as documented in the records). For instance, correlating recent inquiries about medical symptom with past medical data to predict future health progression.

With continued reference to FIG. 1, in some cases, each entity feature, including inquiry feature and record feature may be represented as a vector. In these cases, set of entity features may be represented as a vector space. A "vector," as defined in this disclosure, is a data structure that represents one or more quantitative values and/or measures of a given data element. A vector may be represented as an n-tuple of values, where n is one or more values, as described in further detail below. A "vector space," as defined in his disclosure, is a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. In some cases, two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3].

With continued reference to FIG. 1, vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute 1 as derived using a Pythagorean norm:

$$l = \sqrt{\sum_{i=0}^{n} a_i^2},$$

where ai is attribute number i of the vector. Scaling and/or normalization may function to make vector comparison independent of absolute quantities of attributes, while preserving any dependency on similarity of attributes.

With continued reference to FIG. 1, at least a processor 108 is configured to implement a nested data storage structure 144 to store plurality of inquiries 116 and plurality of entity records 132 based on one or more entity features 136. As used in this disclosure, a "nested data storage structure" is a specific data storage architecture designed to efficiently organize and manage interrelated data. In one embodiment, nested data storage structure 144 may include a structure systematically categorizes data such as plurality of inquiries 116 and plurality of entity records 132 into a hierarchy of containers (or "nests") where each level of the structure may include a plurality of subordinate levels; thus, at least in part, nested data storage structure may enable a logical and intuitive arrangement of data elements based on entity features 136 and relational datums 140 thereof. As a non-limiting example, nested data storage structure 144 may be implemented as a "graph-based database," a type of database that uses graph structures for semantic queries with nodes, edges, and properties represent and store data. In some cases, graph-based database may include a plurality of nodes and a plurality of edges connecting the plurality of nodes, wherein each node of plurality of nodes may represent data points such as, without limitation, plurality of inquiries and/or entity records, and each edge of the plurality of edges may represent a relationship or association between these points based on identified entity feature as described above.

With continued reference to FIG. 1, in one or more embodiments, nested data storage structure 144 may include an implementation of one or more aspects of hierarchical layering. In some cases, plurality of inquiries 116 and plurality of entity records 132 may be aggregated, layered hierarchically, and stored within nested data storage structure 144. Aggregated inquiries and entity records may be organized into a plurality of layers or levels (i.e., nodes), wherein each layer may be designated with a specific types of information or functionality and the plurality of layers in a top-down structure wherein the top layers or root node are more general or abstract and lower layers or leaf node are more detailed or specific. As a non-limiting example, each node of plurality of nodes may include one or more data elements that may act as parents to one or more data elements in the child node or nodes in the layer directly below. In some cases, nested data storage structure 144 may be inherently recursive, for example, and without limitation, same organizational principle applies within each layer of nodes and across the entire structure. Additionally, or alternatively, higher layer of nodes may encapsulate lower layer of nodes below them, therefore, in some cases, changes in leaf nodes may not necessarily impact root nodes.

With continued reference to FIG. 1, aggregating plurality of inquiries 116 and entity records 132 may include paring, for each inquiry of plurality of inquiries 116, at least a portion of entity record as a function of one or more entity features 136. As a non-limiting example, one or more inquiries related to same symptoms may be grouped and stored under a "Symptoms" node, with sub-nodes for each specific symptom that further link to related medical records or treatments. One or more relational datums may be used as pointers carrying semantic meaning e.g., causality, sequence, or priority to connect one layer of nodes to another layer of nodes thereby enabling queries that span multiple layers of node. As a non-limiting example, nested data storage structure 144 may include upper layer nodes representing general health metrics such as "diabetes' and lower layer nodes relating to individual patient's health states, treatments, lab results, and the like. For instance, "blood sugar level" node, "medication adherence" node, and "dietary habits" node may be directly under "diabetes" node. A relational datum may link lower layer node to upper layer node for the same patient, for example, and without limitation, such relation datum may include a semantic meaning indicate an effectiveness of diabetes mediation on blood sugar control may be assessed by examining the connection between corresponding nodes. As another non-limiting example, a second relational datum may link "dietary habit" node to "blood sugar level" node, suggesting an influence of diet on glucose control. At least a processor 108 may execute one or more queries that span multiple layers of nodes, e.g., a query formulated to identify patients whose "medication adherence" is low and correlate data with "blood sugar level" using these relation datums, to evaluate if there is a pattern of poor control among these patients.

With continued reference to FIG. 1, in one or more embodiments, nested data storage structure 144 may employ an indexing mechanism that index aggregated data by relevant entity features. At least a processor 108 may be configured to create indexes based on extracted entity features 136; for instance, and without limitation, for each entity feature, an index may be generated that maps entity feature to corresponding data points or nodes within nested data storage structure 144. As a non-limiting example, if "patient age" and "medication type" are identified as relevant features to a specific type of disease node within nested data storage structure 144, indexing mechanism may be configured to create indexes that enable at least a processor 108 to locate nodes the specific type of disease node efficiently. In one or more embodiments, indexes may be implemented using data structure such as, without limitation, B-trees, hash tables, or inverted indexes. Actual implementation of indexes may depend on the nature of queries system 100 needs to support. For example, and without limitation, B-trees may be used for range queries which are common with numerical data such as age or dates, while hash tables may be efficient for categorical data that often needs to exact match queries. In some cases, once indexes are created, each index may be integrated into corresponding node, allowing computing device 104 to quickly point to the node containing data relevant to particular entity feature.

With continued reference to FIG. 1, as a non-limiting example, at least a processor 108 may receive plurality of inquiries, such a real-time input from patients via a digital platform, e.g., symptom reported through a patient portal, questions about medication side effects submitted through a connected application, requests for appointment scheduling, and/or inquiries about treatment options. In some cases, one or more entity records may be retrieved simultaneously, by at least a processor 108, from one or more digital information repositories such as, without limitation, an EHR system. Such entity records may include, for example, and without limitation, historical medical diagnoses including dates of those diagnoses, treatment plans and outcomes, medication history, laboratory results, medical imaging files, among others. In one or more embodiments, plurality of inquiries may be continuously updated in real-time as patients interact with system 100, while entity records may be periodically synchronized from EHR system. One or more entity features may be extracted from both datasets. In some cases, set of inquiry features, such as, without limitation, frequency of symptom mentions, types of questions asked about medications, urgency indicated in appointment requests, and/or the like may be extracted from plurality of inquiries, and set of record features, such as, without limitation, frequency of specific medical conditions, medication adherence rate, historical treatment effectiveness, and/or the like may be extracted from retrieved entity records. At least a processor 108 may be configured to detect correlations between the set of inquiry features and the set of record features; for instance, and without limitation, it may analyze if patients frequently asking about a specific symptom correlate with a historical diagnosis in their entity records. One or more "symptom" nodes (each represents a specific symptom that patients have inquired about) and "diagnosis" nodes (each represents a type of diagnosis recorded in the entity records) may be created with one or more edges connected between them and indexes associated with each node.

With continued reference to FIG. 1, at least a processor 108 is configured to generate, at one or more process modules 148 interfaced with at least a processor 108, one or more contextual responses 152 upon receipt of an additional inquiry 156 by traversing nested data storage structure 144. As used in this disclosure, a "process module" is a component or a subsystem within a larger software or hardware architecture that is designed to handle a distinct task. One or more process modules 148 may be communicatively connected and coordinate with at least a processor 108 or any other computing device of system 100 to receive one or more data elements for processing and to send back processed results or actions to be executed by system 100. As a non-limiting example, process module 148, interfaced with at least a processor 108 through one or more APIs (or direct memory access), may be dedicated to carrying out a specific function or a set of functions within system 100 such as data analysis, query processing, machine learning, or any other processing steps as described herein. Exemplary process module may include, without limitation, NLP module, large language model (LLM), recommendation engine, data analytics module, real-time monitoring module, verification module, and/or any other third party modules that may be integrated into the system.

With continued reference to FIG. 1, as used in this disclosure, a "contextual response" is a generated reply or output corresponding to a received inquiry that is specifically tailored to situations, needs, and background of associated entity or the received inquiry. In one embodiment, contextual response may not be a generic or static inquiry response, but a dynamically crafted answer (based on relevant entity features 136, user interactions, or other information pertaining to entity 120 or received inquiry that have been identified and processed by system 100 as described herein). In some cases, contextual response 152 may include a hypothesis supported by plurality of inquiries 116, entity records 132, and/or other contextual information related to entity 120 or the environment. In some cases, contextual response 152 may be specifically relevant to a current situation or need of entity 120. As a non-limiting example, system 100 may be configured to interpret user's intent, preferences, or past interactions, using NLP module as described above and render a contextual response considering interpreted user's intent, preferences, or paster interactions at one or more interfaced process modules 148, such as, without limitation, a LLM as described below. In some cases, contextual response 152 may be adaptive; for instance, without limitation, contextual response 152 may reflect any changes in underlying data or evolving user requirements. As additional data is ingested and processed by system 100 and connected process module, a first contextual response may be updated or a second contextual response addressing the discrepancies may be generated by the process module. For example, and without limitation, contextual response 152 may be part of an ongoing interaction with entity 120. In some cases, such contextual response 152 may prompt further dialogue, request for additional information, or adjust itself based on user's feedback.

With continued reference to FIG. 1, as used in this disclosure, an "additional inquiry" is a subsequent or follow-up query submitted by an entity after initial interactions or plurality of inquiries 116 transactions have already occurred within system 100. As a non-limiting example, if user inquiries about symptom management for a chronic condition, system 100 may assess such inquiry against user's medical history and current treatment protocol within nested data storage structure 144 in accordance by traversing nested data storage structure 144 to provide a response that not only addresses user's inquiry but also considered user's specific health status and prior responses to historical treatments. Additionally, or alternatively, system 100 may be configured to enrich, as part of contextual response 152 or entirely based upon contextual response 152, a first entity's record, such as a user health profile within a third party database, by integrating one or more data elements incorporated within contextual response 152 generated based on real-time inquiries with background provided by a second entity record, such as a creditable EHR retrieved from a trusted medical repository. For example, and without limitation, user health profile may be updated based on symptom frequency or adjusting medication plans based on questions about one or more side effects.

With continued reference to FIG. 1, in some cases, upon receipt of additional inquiry 156 at one or more process modules 148, such as, without limitation, a user asking for further clarification on a previously suggested treatment after reviewing initial recommendations provided by process module 148 such as a recommendation engine configured to create personalized treatment plan, at least a processor 108 may be configured to traverse nested data storage structure 144. In one embodiment, traversing nested data storage structure 144 may include moving, based on relational datums (e.g., symptom-to-disease correlations) and the context of additional inquiry 156, layers or nodes of nested data storage structure 144 containing plurality of entity records 132 or data referring entity records 132, from more generalized nodes to more specific nodes. In some cases, at termination of the said traversal, system 100 may point at one or more nodes that are most relevant to additional inquiry 156. As a non-limiting example, if an inquiry relates to a specific symptom, system 100 may associate medical conditions, previous diagnostic outcomes, or relevant patient demographics retrieved from user's EHR to the inquiry and generate a symptom node within nested data storage structure 144. Such symptom node may include an entity feature that acts as a key for a subsequent traversal during the generation of contextual response 152. Throughout the traversal, at least a processor 108 may analyze relational datums thereof that connect different entity features across the nested data storage structure 144. For instance, if an additional inquiry involves the same symptom, relational datums may be used to explore connections to potential disease, treatment histories, and other related symptoms efficiently; thus, a more comprehensive profile of the additional inquiry incorporating all relevant entity record and other contextual data may be compiled and system 100 may then generate, at a process module such as an LLM as described below, a contextual response leveraging such compiled information.

With continued reference to FIG. 1, in one or more embodiments, process modules 148 may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, or any of the combinations thereof. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if a user has already typed the words "how should I manage" and the user's medical records indicate a history of diabetes, LLM may consider this context to predict the next word. In this cases, it may be highly likely that the words "may blood sugar" will come next. In some embodiments, LLM may output predictions by ranking phrases by likelihood based on the context e.g., entity record such as user's EHR, therefore, LLM may score, in this example, "my blood sugar" as the most likely continuation, "my diet" as the next most likely, and "my medication" thereafter.

With continued reference to FIG. 1, in one or more embodiments, LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, in some cases, an LLM and/or transformer architecture may include an attention mechanism. An "attention mechanism," as used herein, is a part of a neural architecture that enables a system to dynamically quantify the relevant features such as inquiry features of one or more input inquiries. In the case of natural language processing, input inquiries may be a sequence of textual elements. It may be applied directly to the raw input or to its higher-level representation. In an embodiment, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

With continued reference to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may consider all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may be trained to use self-attention to analyze sentence structure of user input e.g., "what are the side effects of" and produce a likely continuation based on associated medical context. In some embodiments, to achieve self-attention, input may be fed into three distinct fully connected neural network layers to create query or inquiry, key, and value vectors. In some cases, in this non-limiting example, query or inquiry vectors may represent user input seeking information relevant to "side effects," key vectors may correspond to possible matching words or phrases in dataset (including user's historical inquiries and user's medical data), such as "medication," "treatment," "drug name," and any other words or phrase that are typically followed by a list of effects or concerns, and value vectors may carry the actual information about the side effects associated with the key vectors' corresponding medical terms. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input. In some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "symptom [of]," decoder should not have access to the word related to one or more particular diseases, because that word is a future word that was generated after. The word "of" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens".

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word. Decoder may take this output and add it to the decoder inputs. Decoder may continue decoding until a token is predicted. Decoder may stop decoding once it predicts an end token. In some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, as a non-limiting example, process module 148 such as an LLM may receive an inquiry from entity 120. Inquiry may include a string of one or more characters. For example, inquiry may include a user input containing one or more words, sentences, paragraphs that poses one or more questions. In some embodiments, inquiry may be received from a user device i.e., any computing device that is used by a user, such as, without limitation, desktops, laptops, smartphones, tablets, and the like. In some embodiments, inquiry may include one or more medical questions asked by a patient. LLM may generate at least one annotation as an output. At least one annotation may include at least a portion of contextual response as described above. In some embodiments, an LLM may include multiple sets of transformer architecture as described above. In some cases, output may include a textual output, for example, and without limitation, textual output may include a phrase or sentence identifying an answer to the medical questions asked by the patient.

With continued reference to FIG. 1, in some embodiments, generating contextual responses 152 may include initializing a response template as a function of additional inquiry 156. As used in this disclosure, a "response template" is a data structure defining a pre-defined framework used to structure and format responses generated by one or more process modules 148. In some cases, response template may act as a scaffold for final response, where specific content may be dynamically filled in based on data derived from user interactions and relevant background information. In one embodiment, response template may include a plurality of placeholders or variables that are populated with data retrieved during the traversal of nested data storage structure 144 based on additional inquiry 156. In another embodiment, response template may include an empty list or data structure that awaits for the result of the data traversal of the structure. In other embodiments, response template may include a framework that structures data input to process modules 148. In some cases, at least a processor 108 may be configured to select or generate a response template that correspond to the type of inquiry received, for example, and without limitation, if the inquiry pertains to a medical diagnosis, the response template may include sections for symptoms, predicted conditions, recommend treatments, follow-up questions, and/or the like. As at least a processor 108 navigates through nested data storage structure 144, initial response template may be expanded based on relevant aggregated data retrieved that correspond to entity feature that linked to additional inquiry 156. For example, and without limitation, one or more nodes having matched entity feature within nested data storage structure 144 may be iteratively duplicated, de-referenced, and/or appended to response template. Response template may include a tree or a linked list, wherein each element (or node) represent a part of the response, structured hierarchically or sequentially based on the flow of information. In some cases, such traversal may allow system 100 to fill in plurality of placeholders or variables in response template with specific data points, for example, and without limitation, identified symptoms, correlated medical conditions, or historical health data pertinent to additional inquiry 156, making response template specific to the inquiry context and user's entity records. Once nested data storage structure 144 has been traversed, at least a processor 108 may then fed the expanded response template into one or more designated process modules that are designed to process the populated template further using, for example, one or more machine learning algorithms as described herein to generate one or more contextual responses 152. In some cases, contextual response may be previously generated and refined by response template. Designated process modules may include one or more machine learning models trained using training data containing a plurality of response templates as input and correlated to a plurality of contextual responses as output.

With continued reference to FIG. 1, in some cases, process modules 148 may include an integrated predictive diagnostic tool. In some embodiments, one or more contextual responses 152 may include a diagnosis prediction, wherein the "diagnosis prediction," for the purpose of this disclosure, is a forecast or determination made by a system regarding a likelihood or presence of a medical condition, disease, or disorder in an entity, based on received data. In some cases, diagnosis prediction may anticipate a medical diagnosis digitally based on available data e.g., data selected during the traversal of nested data storage structure 144 as described above based on at least one entity feature, rather then confirming the medical diagnosis through direct medical testing. Such diagnosis prediction may be expressed in terms of probabilities or likelihood, providing entity 120 e.g., a patient or other associated entities such as physicians of the patient with an estimated risk level of certain medical conditions based on historical inquiries in addition to patient's EHR on record. In one or more embodiments, process modules 148 may include at least a diagnosis model interfaced with at least a processor 108 through one or more APIs, wherein the "diagnosis model," for the purpose of this disclosure, is a specialized component of a healthcare system's processing capabilities. In some cases, at least a diagnosis model may be implemented as part of an LLM or another processing module. As a non-limiting example, at least a diagnosis model may implement any machine learning algorithm as described herein such as a neural network that is trained using diagnosis training data containing a plurality of medical data as input correlated with a plurality of diagnosis predictions as output. In some cases, system 100 may fine-tune at least a diagnosis model according to specific entity feature e.g., medical criteria, demographic considerations, changes in treatment protocol, or the like.

With continued reference to FIG. 1, as a non-limiting example, at least a diagnosis model may be specifically trained on response templates containing historical patient inquiries, patient symptoms, medical history, and other relevant contextual data retrieved from nested data storage structure 144. As diagnosis model traverses through the stored data, it may apply learned features and medical knowledge bases to generate a contextual response containing a diagnosis prediction. For instance, if a patient presents with symptoms of fever, headache, and a rash, such diagnosis model evaluates these inputs against known disease profiles for infections like meningitis or Lyme disease and generate a likelihood of each condition based on the aggregated data. Additionally, or alternatively, based on the populated response template, diagnosis model may also generate recommendations for a second entity 160 such as, without limitation, healthcare provider of the patient. For instance, if a patient frequently inquiries about pain relief and has a history of chronic pain management, system 100 may suggest revisiting the patient's pain management plan. In some embodiments, contextual responses 152 may include one or more identifications of trends or anomalies that may not be visible through one type of data alone.

With continued reference to FIG. 1, additionally, or alternatively, at least a processor 108 may be configured to modify, as a function of one or more contextual responses 152, nested data storage structure 144. In one embodiment, structure organization, relationships between nodes (i.e., edges), and nodes themselves within nested data storage structure 144 may be dynamically updated or altered based on contextual responses 152 containing, for example, information regarding what system 100 learns or decides through any foregoing processing of later received additional inquiry 156 and generation of responses. As a non-limiting example, at least a processor 108 may receive feedbacks on one or more contextual responses generated by process modules 148 such as diagnosis model as described above regarding the output's accuracy, relevancy, effectiveness of suggested actions, and/or the like. For instance, if one or more repeated contextual responses 152 indicate a frequent misclassification of symptom to disease, system 100 may adjust one or more relational datums or positioning of edges between one or more nodes in question within nested data storage structure 144. As a non-limiting example, system 100 may initially response with certain responses covering a broad category of respiratory disease. If over time, additional inquiries 156, contextual responses 152, and possibly user feedback suggest a high prevalence of specific condition such as asthma, system 100 may modify nested data structure to separate nodes related to asthma into a more distinct category within its own unique set of symptoms and treatments. As another example, if new data is added or existing node is modified within nested data storage structure 144, indexes may be updated accordingly to reflect most recent state of the storage structure thereby maintaining query accuracy. In some cases, system 100 may employ techniques such as incremental indexing or real-time index updates to manage changes efficiently.

Still referring to FIG. 1, at least a processor 108 may be configured to display one or more contextual responses 152 to entity 120 through a user interface 164 at a display device 168. As used in this disclosure, a "display device" refers to an electronic device that visually presents information to an entity. In some cases, display device may be configured to project or show visual content generated by computers, video devices, or other electronic mechanisms. In some cases, display devices may include, without limitation, a liquid crystal display (LCD), a cathode ray tube (CRT), a plasma display, a light emitting diode (LED) display, and any combinations thereof. In a non-limiting example, one or more display devices may vary in size, resolution, technology, and functionality. Display device may be able to show any data elements and/or visual elements as listed above in various formats such as, textural, graphical, video among others, in either monochrome or color. In one or more embodiments, at least a processor 108 may be connected to display device 184.

With continued reference to FIG. 1, as used in this disclosure, a "user interface" is a digital display that configures a display device to present information, options, interactive elements to users in an intuitive and visually appealing manner. In some embodiments, user interface 164 may include at least an interface element. As used in this disclosure, "at least an interface element" is a portion of user interface 164. In a non-limiting example, at least an interface element may include, without limitation, a button, a link, a checkbox, a text entry box and/or window, a drop-down list, a slider, or any other interface element that may occur to a person skilled in the art upon reviewing the entirety of this disclosure. In some embodiments, at least an interface element may include an event handler. An "event handler," as used in this disclosure, is a module, data structure, function, and/or routine that performs an action on remote device in response to a user interaction with event handler graphic. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to a user in response to such requirements.

With continued reference to FIG. 1, in some cases, event handler may include a cross-session state variable. As used herein, a "cross-session state variable" is a variable recording obfuscated data elements generated by at least a processor 108 during a previous session. Such data may include, for instance, previously entered text, previous selections of one or more elements as described above, or the like. For instance, and without limitation, cross-session state variable data may represent a request of data process module initiated in a past session. Cross-session state variable may be saved using any suitable combination of client-side data storage on remote device and server-side data storage connected to processor 108. In some cases, contextual responses 152 may be saved wholly or in part as a "cookie" which may include data or an identification of process module to prompt provision of cross-session state variable by processor 108, which may be store in a database at the process module. In some cases, cross-session state variable may include at least a prior session datum. A "prior session datum" may include any element of data that may be stored in a cross-session state variable. In an embodiment, user interface 164 may be configured to display the at least a prior session datum, for instance and without limitation auto-populating user query data from previous sessions.

With continued reference to FIG. 1, as a non-limiting example, user interface 164 may include a graphical user interface. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
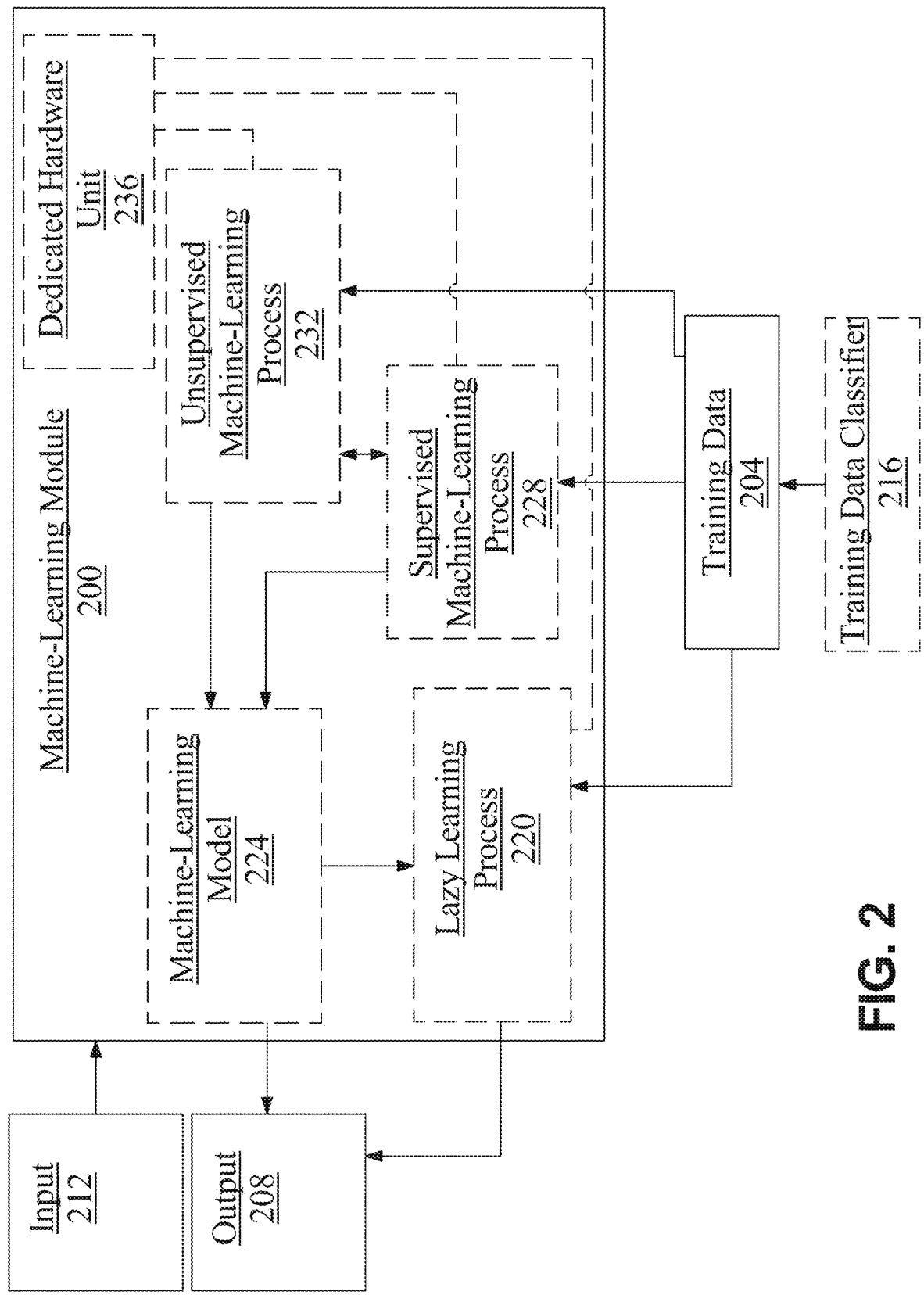
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, training data may include a plurality of response templates as input correlated to a plurality of contextual responses as output.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to [something that characterizes a sub-population, such as a cohort of persons and/or other analyzed items and/or phenomena for which a subset of training data may be selected].

Still referring to FIG. 2, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively, or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively, or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include plurality of response templates as described above as inputs, plurality of contextual response as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
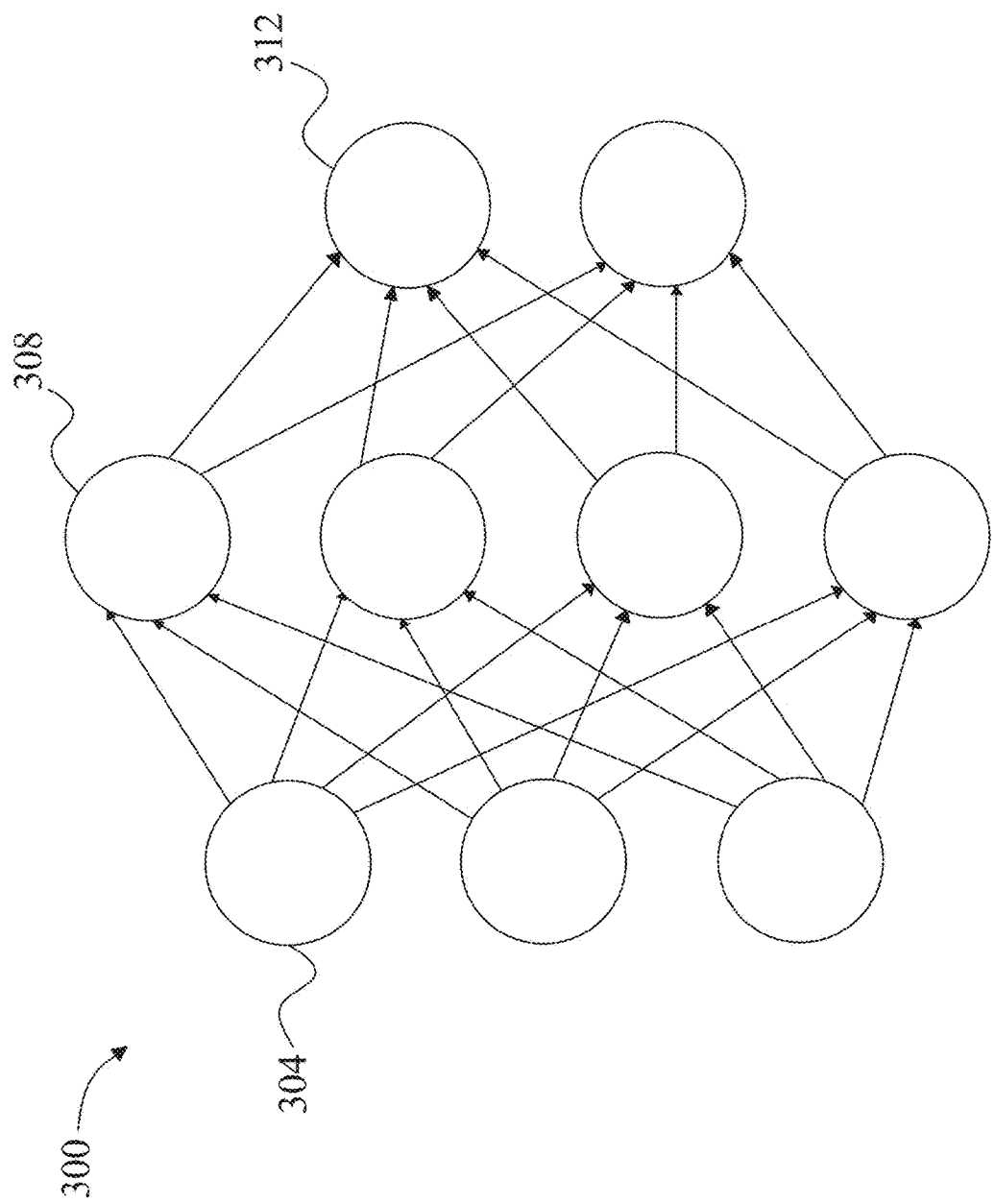
FIG. 3 is a diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network".

With continued reference to FIG. 3, as a further non-limiting example, a neural network may include a convolutional neural network comprising an input layer of nodes, one or more intermediate layers, and an output layer of nodes. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data through a sliding window approach. In some cases, convolution operations may enable processor 108 to detect local/global patterns, edges, textures, and any other features described herein within plurality of private data elements. Detected patterns and/or features may be passed through one or more activation functions, such as without limitation, Rectified Linear Unit (ReLU). Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the dimensions of feature maps by applying downsampling, such as max-pooling or average pooling, to small, non-overlapping regions of one or more features. CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, contextual responses as described above. Additionally, or alternatively, each fully connected layer may be followed by one or more dropout layers configured to prevent overfitting, and one or more normalization layers to stabilize the learning process described herein. Training a CNN may include selecting a suitable loss function to guide the training process. In a non-limiting example, a loss function that measures the difference between the predicted output and the ground truth may be used, such as, without limitation, mean squared error (MSE) or a custom loss function may be designed for one or more embodiments described herein. Additionally, or alternatively, optimization algorithms, such as stochastic gradient descent (SGD), may then be used to adjust the model parameters to minimize such loss.

Figure 4:
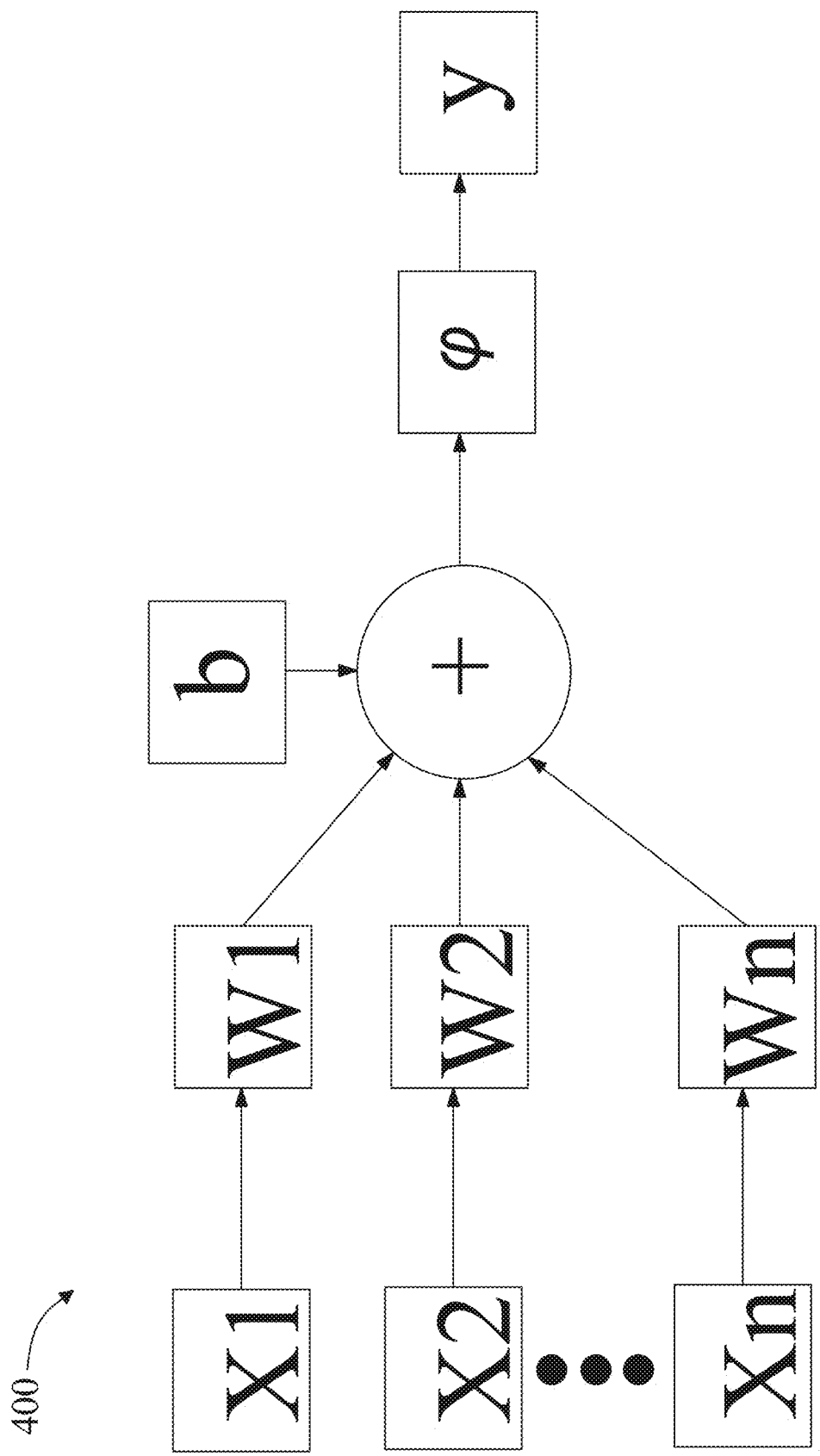
FIG. 4 is a diagram of an exemplary embodiment of a node of a neural network.

Referring now to FIG. 4, an exemplary embodiment of a node 400 of a neural network is illustrated. A node may include, without limitation, a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
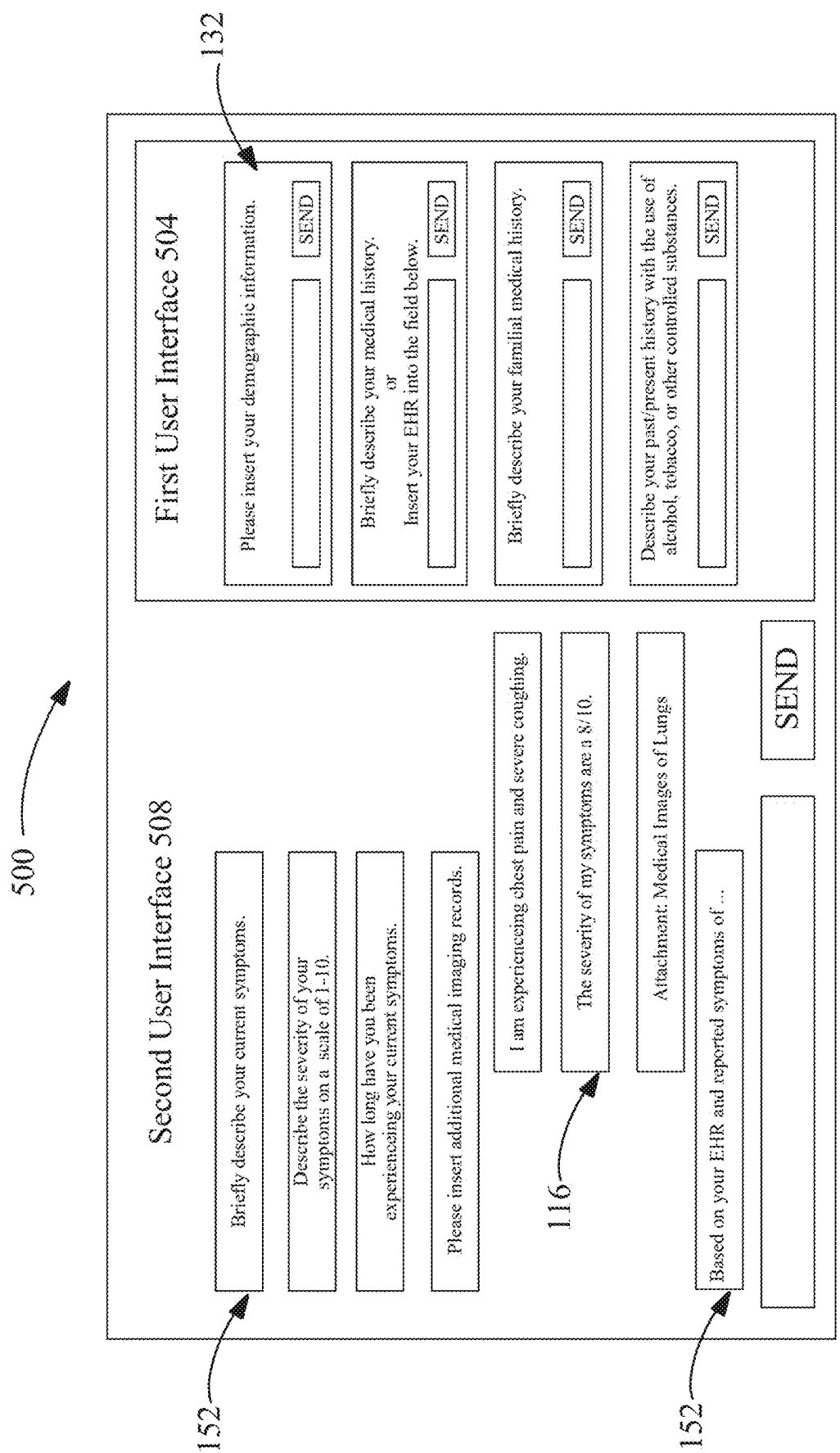
FIG. 5 is an illustration of an exemplary embodiment of a plurality of user interfaces.

Referring now to FIG. 5, an exemplary embodiment of a plurality of user interfaces 500 is illustrated. As used in the current disclosure, a "user interface" is the point of interaction between a user and a digital system or device. A user interface may include elements and mechanisms that enable users to interact with and control the system, application, or software in a visually understandable and intuitive manner. The primary goal of a user interface is to enhance user experience by presenting information in a clear, efficient, and aesthetically pleasing way. FIG. 5 depicts at least two distinct user interfaces, a first user interface 504 and a second user interface 508, respectively. The first user interface 504 may be configured to allow the user to submit information associated with entity records 132 via one or more input fields. Input fields may include text boxes, dropdown menus, buttons, icons, and the like. The input fields of the first user interface 504 may allow the user to submit text, images, audio, documents, video, and the like. The first user interface 504 may allow the user to submit, adjust, or modify portions of entity records 132, The second user interface 508 may take the form of a chatbot, as discussed in greater detail below, to submit plurality of inquiries 116. Additionally, the second user interface 308 may allow the user to respond to one or more system-generated questions by submitting plurality of inquiries 116. The user may submit plurality of inquiries 116 using one or more input fields. In some cases, the second user interface 508 may be communicatively connected to at least a processor 108. In some cases, plurality of inquiries 116 may also include captured images, recorded videos, or audios, and the like. In some cases, one or more contextual responses 152 may be displayed in second user interface 508. In some cases, user may reply to contextual responses 152 through one or more inquiries. For example, and without limitation, a user may submit user feedback to contextual responses 152 or, in other cases, be connected via audio or video call to second entity 120 such as a medical professional through plurality of user interfaces 500 based on contextual responses 152.

Figure 6:
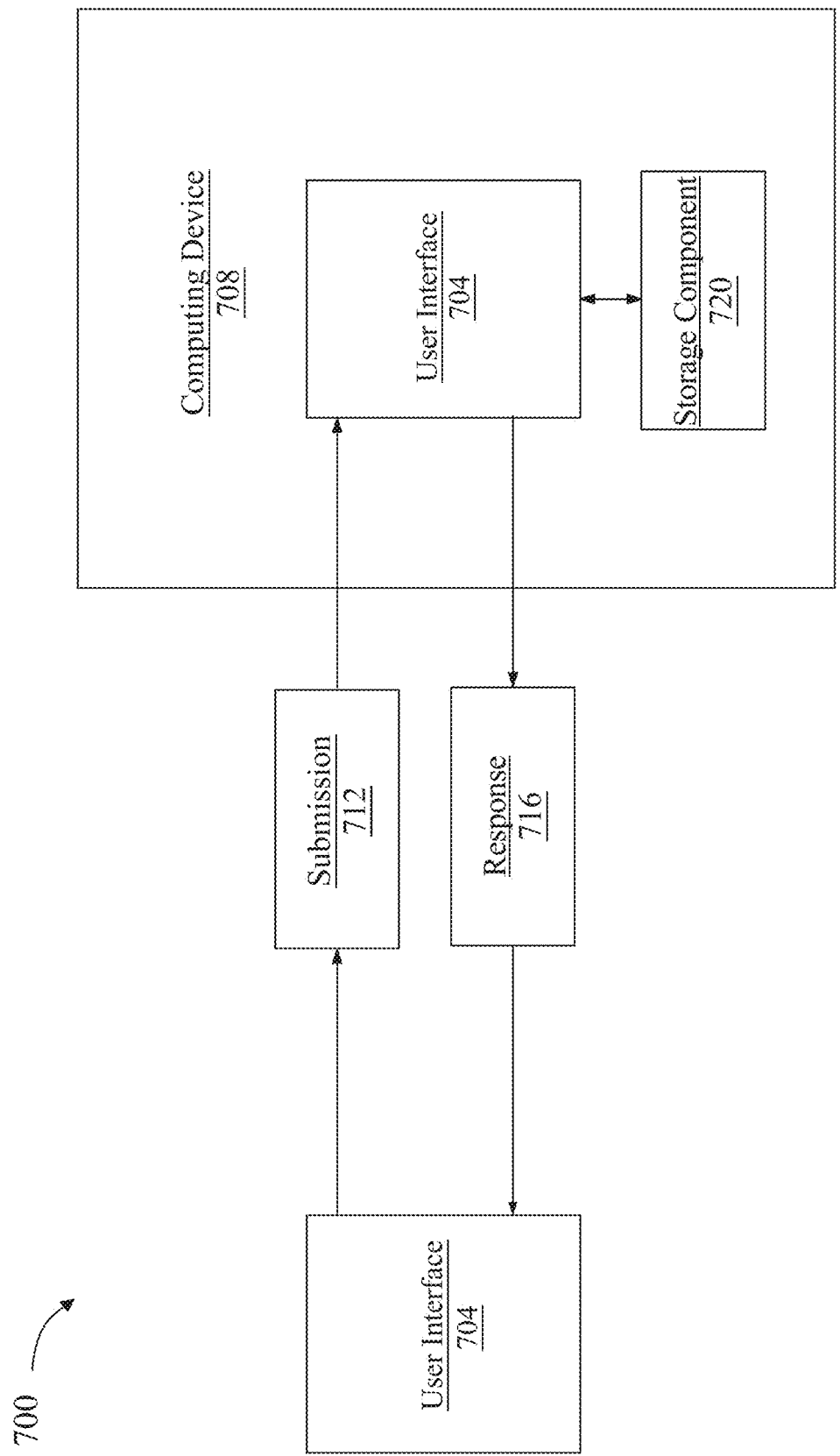
FIG. 6 is an illustration of an exemplary embodiment of a chatbot.

Referring to FIG. 6, a chatbot system 600 is schematically illustrated. According to some embodiments, a user interface 604 may be communicative with a computing device 608 that is configured to operate a chatbot. In some cases, user interface 604 may be local to computing device 608. Alternatively, or additionally, in some cases, user interface 604 may remote to computing device 608 and communicative with the computing device 608, by way of one or more networks, such as without limitation the internet. Alternatively, or additionally, user interface 604 may communicate with user device 608 using telephonic devices and networks, such as without limitation fax machines, short message service (SMS), or multimedia message service (MMS). Commonly, user interface 604 communicates with computing device 608 using text-based communication, for example without limitation using a character encoding protocol, such as American Standard for Information Interchange (ASCII). Typically, a user interface 604 conversationally interfaces a chatbot, by way of at least a submission 612, from the user interface 608 to the chatbot, and a response 616, from the chatbot to the user interface 604. In many cases, one or both submission 612 and response 616 are text-based communication. Alternatively, or additionally, in some cases, one or both of submission 612 and response 616 are audio-based communication.

Continuing in reference to FIG. 6, a submission 612 once received by computing device 608 operating a chatbot, may be processed by a processor. In some embodiments, processor processes a submission 612 using one or more keyword recognition, pattern matching, and natural language processing. In some embodiments, processor employs real-time learning with evolutionary algorithms. In some cases, processor may retrieve a pre-prepared response from at least a storage component 620, based upon submission 612. Alternatively, or additionally, in some embodiments, processor communicates a response 616 without first receiving a submission 612, thereby initiating conversation. In some cases, processor communicates a query to user interface 604; and the processor is configured to process an answer to the query in a following submission 612 from the user interface 604. In some cases, an answer to a query present within submission 612 from a user device 604 may be used by computing device 608 as an input to another function.

Figure 7:
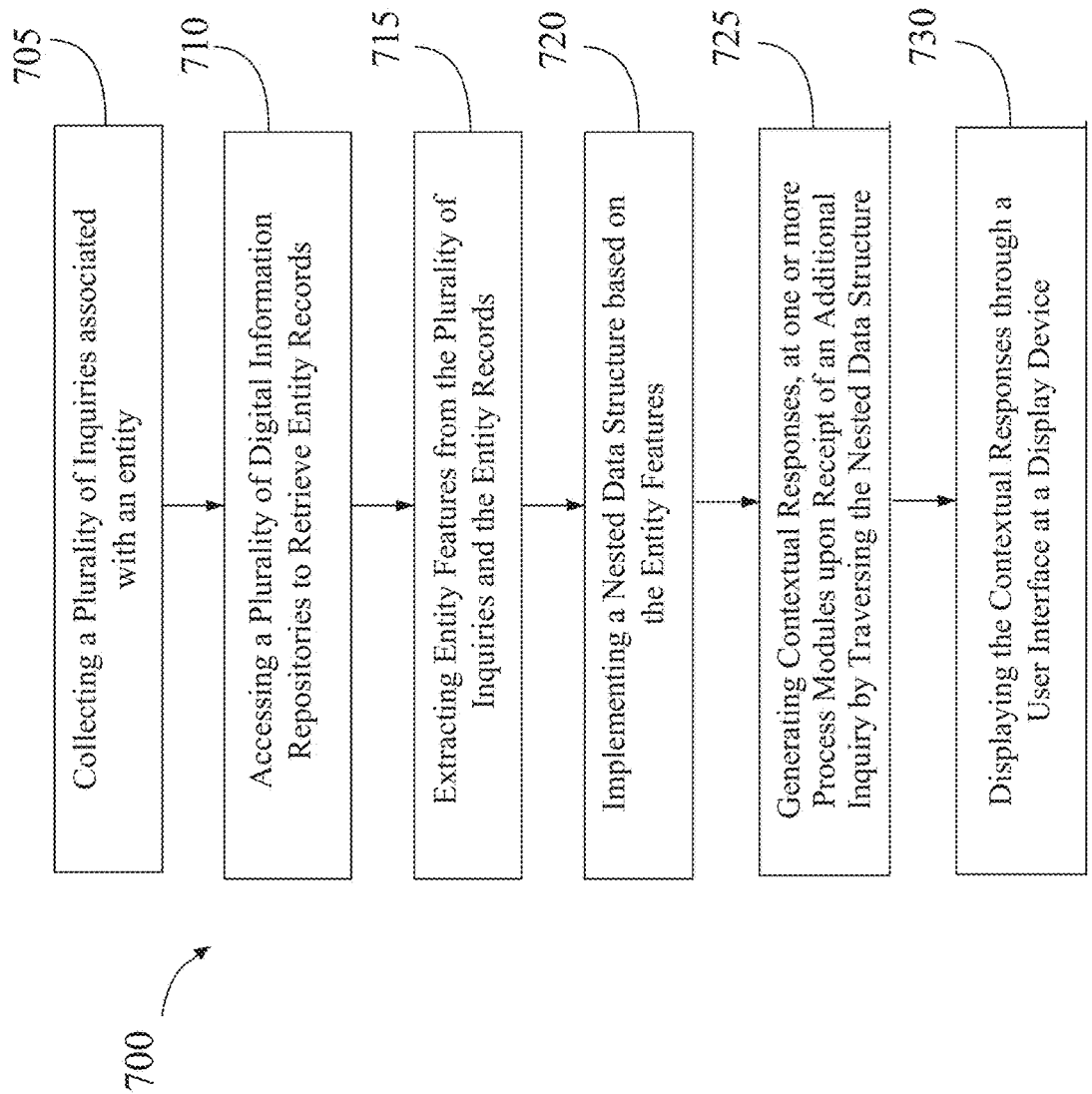
FIG. 7 is a flow diagram illustrating an exemplary method for delivering contextual response through dynamic integrations of digital information repositories with inquiries.

Now referring to FIG. 7, a flow diagram of an exemplary embodiment of a method 700 for delivering contextual responses through dynamic integrations of digital information repositories with inquiries is illustrated. Method 700 includes a step 705 of collecting, by at least a processor, a plurality of inquiries associated with an entity. In some embodiments, each inquiry of the plurality of inquiries may include a structured data input describing at least one user-generated question. In some embodiments, collecting the plurality of inquiries may include generating the plurality of inquiries as a function of entity activity data pertaining to the entity. This may be implemented without limitation, as described above with reference to FIGS. 1-6.

With continued reference to FIG. 7, method 700 includes a step 710 of accessing, by the at least a processor, a plurality of digital information repositories in communication with the at least a processor to retrieve a plurality of entity records pertaining to the entity. In some embodiments, plurality of entity records may include an electronic health record (EHR). This may be implemented without limitation, as described above with reference to FIGS. 1-6.

With continued reference to FIG. 7, method 700 includes a step 715 of extracting, by the at least a processor, one or more entity features from the plurality of inquiries and the plurality of entity records. In some embodiments, extracting the one or more entity features may include extracting a set of inquiry features from the plurality of inquiries, extracting a set of record features from the plurality of entity records, and identifying the one or more entity features by correlating the set of inquiry features and the set of record features. In some embodiments, each entity feature of the one or more entity features may include at least a relational datum. This may be implemented without limitation, as described above with reference to FIGS. 1-6.

With continued reference to FIG. 7, method 700 includes a step 720 of implementing, by the at least a processor, a nested data storage structure to store the plurality of inquiries and the plurality of entity records based on the one or more entity features. In some embodiments, the nested data storage structure may include a graph-based database having a plurality of nodes and edges connecting the plurality of nodes. This may be implemented without limitation, as described above with reference to FIGS. 1-6.

With continued reference to FIG. 7, method 700 includes a step 725 of generating, by the at least a processor, one or more contextual responses, at one or more process modules interfaced with the at least a processor, upon receipt of an additional inquiry by traversing the nested data storage structure. In some embodiments, generating one or more contextual responses may include initializing a response template as a function of the additional inquiry, expanding, based on the traversal of the nested data storage structure, the response template, and feeding the response template to the one or more process models to generate the one or more contextual responses. In some embodiments, the one or more contextual responses may include a diagnosis prediction, and the one or more processor models may include at least a diagnosis model configured to generate the diagnosis prediction as a function of at least an entity feature of the one or more entity features traversed in the nested data storage structure. This may be implemented without limitation, as described above with reference to FIGS. 1-6.

With continued reference to FIG. 7, method 700 includes a step 730 of displaying, by the at least a processor, the one or more contextual responses to the entity through a user interface at a display device. Method 700 may further include a step of modifying the nested data storage structure as a function of the one or more contextual responses. This may be implemented without limitation, as described above with reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
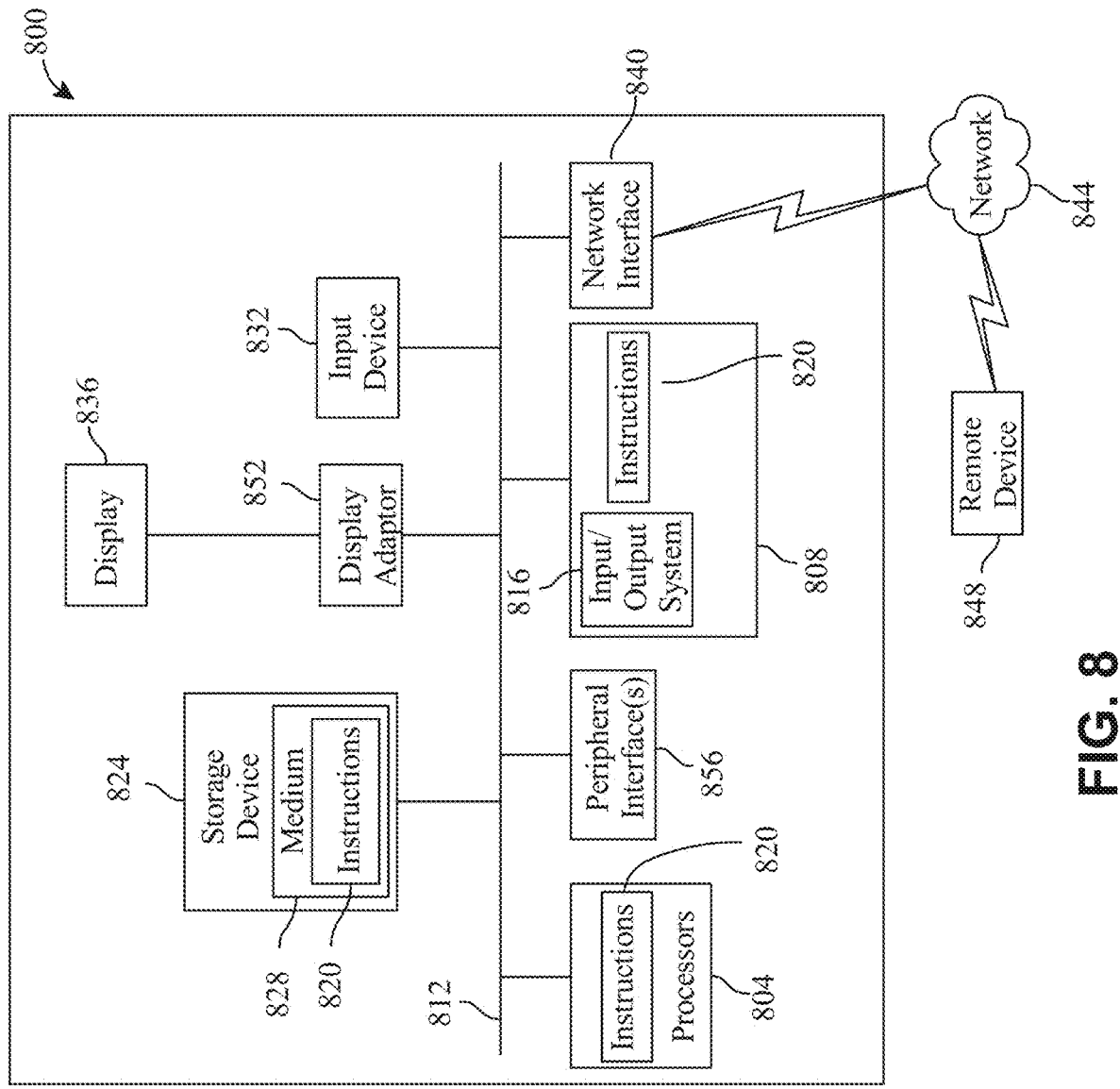
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for delivering contextual responses through dynamic integrations of digital information repositories with inquiries, the system comprising:
a computing device having at least a processor and a memory communicatively connected to the at least a processor, wherein the memory contains instructions configuring the at least a processor to:
collect a plurality of inquiries associated with an entity;
access a plurality of digital information repositories in communication with the at least a processor to retrieve a plurality of entity records pertaining to the entity;
update, in real-time, the plurality of inquiries as a function of patient interactions, wherein the processor receives real-time inputs from an entity via a digital platform;
extract one or more entity features from the plurality of inquiries and the plurality of entity records;
generate a nested data storage structure to store the plurality of inquiries and the plurality of entity records based on the one or more entity features, wherein the nested data storage structure comprises at least a symptom node and at least a diagnosis node, wherein the symptom node represents a symptom that an entity has inquired about, wherein the diagnosis node represents a diagnosis recorded in the plurality of entity records;
generate, at one or more process modules interfaced with the at least a processor, one or more contextual responses upon receipt of an additional inquiry by traversing the nested data storage structure, wherein generating the one or more contextual responses comprises:
   initializing a response template as a function of the additional inquiry;
   expanding, based on the traversal of the nested data storage structure, the response template; and
   feeding the response template to the one or more process modules to generate the one or more contextual response; and
display the one or more contextual responses to the entity through a user interface at a display device, wherein the user submits user feedback to the contextual responses, wherein the user feedback is used to update the plurality of inquiries.

2. The system of claim 1, wherein each inquiry of the plurality of inquiries comprises a structured data input describing at least one user-generated question.

3. The system of claim 1, wherein collecting the plurality of inquiries comprises generating the plurality of inquiries as a function of entity activity data pertaining to the entity.

4. The system of claim 1, wherein the plurality of entity records comprises an electronic health record (EHR).

5. The system of claim 1, wherein extracting the one or more entity features comprises:
   extracting a set of inquiry features from the plurality of inquiries;
   extracting a set of record features from the plurality of entity records; and
   identifying the one or more entity features by correlating the set of inquiry features and the set of record features.

6. The system of claim 1, wherein each entity feature of the one or more entity features comprises at least a relational datum.

7. The system of claim 1, wherein the nested data storage structure comprises a graph-based database having a plurality of nodes and edges connecting the plurality of nodes.

8. The system of claim 1, wherein:
   the one or more contextual responses comprises a diagnosis prediction; and
   the one or more process modules comprises at least a diagnosis model configured to generate the diagnosis prediction as a function of at least an entity feature of the one or more entity features traversed in the nested data storage structure.

9. The system of claim 1, wherein the memory further contains instructions configuring the at least a processor to modify the nested data storage structure as a function of the one or more contextual responses.

10. A method for delivering contextual responses through dynamic integrations of digital information repositories with inquiries, the method comprising:
   collecting, by at least a processor, a plurality of inquiries associated with an entity;
   accessing, by the at least a processor, a plurality of digital information repositories in communication with the at least a processor to retrieve a plurality of entity records pertaining to the entity;
   updating, in real-time, the plurality of inquiries as a function of patient interactions, wherein the processor receives real-time inputs from an entity via a digital platform;
   extracting, by the at least a processor, one or more entity features from the plurality of inquiries and the plurality of entity records;
   generating, by the at least a processor, a nested data storage structure to store the plurality of inquiries and the plurality of entity records based on the one or more entity features, wherein the nested data storage structure comprises at least a symptom node and at least a diagnosis node, wherein the symptom node represents a symptom that an entity has inquired about, wherein the diagnosis node represents a diagnosis recorded in the plurality of entity records;
   generating, by the at least a processor, one or more contextual responses, at one or more process modules interfaced with the at least a processor, upon receipt of an additional inquiry by traversing the nested data storage structure, wherein generating the one or more contextual responses comprises:
      initializing a response template as a function of the additional inquiry;
      expanding, based on the traversal of the nested data storage structure, the response template; and
      feeding the response template to the one or more process modules to generate the one or more contextual responses; and
   displaying, by the at least a processor, the one or more contextual responses to the entity through a user interface at a display device, wherein the user submits user feedback to the contextual responses, wherein the user feedback is used to update the plurality of inquiries.

11. The method of claim 10, wherein each inquiry of the plurality of inquiries comprises a structured data input describing at least one user-generated question.

12. The method of claim 10, wherein collecting the plurality of inquiries comprises generating the plurality of inquiries as a function of entity activity data pertaining to the entity.

13. The method of claim 10, wherein the plurality of entity records comprises an electronic health record (EHR).

14. The method of claim 10, wherein extracting the one or more entity features comprises:
   extracting a set of inquiry features from the plurality of inquiries;
   extracting a set of record features from the plurality of entity records; and
   identifying the one or more entity features by correlating the set of inquiry features and the set of record features.

15. The method of claim 10, wherein each entity feature of the one or more entity features comprises at least a relational datum.

16. The method of claim 10, wherein the nested data storage structure comprises a graph-based database having a plurality of nodes and edges connecting the plurality of nodes.

17. The method of claim 10, wherein:
   the one or more contextual responses comprises a diagnosis prediction; and
   the one or more process modules comprises at least a diagnosis model configured to generate the diagnosis prediction as a function of at least an entity feature of the one or more entity features traversed in the nested data storage structure.

18. The method of claim 10, further comprises modifying the nested data storage structure as a function of the one or more contextual responses.

* * * * *